(12) United States Patent
Budzelaar et al.

(10) Patent No.: US 11,877,786 B2
(45) Date of Patent: *Jan. 23, 2024

(54) ENERGY APPLICATION APPARATUS

(71) Applicant: KONINKLIJKE PHILIPS N.V., Eindhoven (NL)

(72) Inventors: Franciscus Paulus Maria Budzelaar, Eindhoven (NL); Godefridus Antonius Harks, Rijen (NL); Steven Antonie Willem Fokkenrood, 'S-Hertogenbosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 413 days.

This patent is subject to a terminal disclaimer.

(21) Appl. No.: 17/126,131

(22) Filed: Dec. 18, 2020

(65) Prior Publication Data

US 2021/0100602 A1 Apr. 8, 2021

Related U.S. Application Data

(63) Continuation of application No. 14/391,182, filed as application No. PCT/IB2013/052808 on Apr. 9, 2013, now Pat. No. 10,874,449.

(Continued)

(51) Int. Cl.
*A61B 18/12* (2006.01)
*A61B 18/14* (2006.01)
(Continued)

(52) U.S. Cl.
CPC .......... *A61B 18/12* (2013.01); *A61B 18/1492* (2013.01); *A61B 90/06* (2016.02); *A61B 2018/00577* (2013.01); *A61B 2018/00642* (2013.01); *A61B 2018/00827* (2013.01); *A61B 2018/00898* (2013.01);
(Continued)

(58) Field of Classification Search
CPC ........................... A61B 18/12; A61B 18/1492
See application file for complete search history.

(56) References Cited

U.S. PATENT DOCUMENTS

| 4,651,280 A | 3/1987 | Chang |
| 4,860,745 A | 8/1989 | Farin |

(Continued)

FOREIGN PATENT DOCUMENTS

| EP | 1169974 | 1/2002 |
| JP | 106273455 A | 9/1994 |

(Continued)

*Primary Examiner* — Joseph M Dietrich

(57) ABSTRACT

An energy application apparatus applies energy to an object. An energy application unit applies energy to the object, wherein the energy application unit is adapted to use electrical current for applying the energy. A current measuring unit measures the electrical current used by the energy application unit and provides a signal being indicative of whether the energy is applied to the object based on the measured electrical current. The signal can be used by, for instance, a monitoring unit and/or a display unit for using and/or indicating the information whether energy is actually applied or not, without requiring a direct communication between the energy application unit and the monitoring unit and/or the display unit.

14 Claims, 6 Drawing Sheets

Related U.S. Application Data

(60) Provisional application No. 61/635,357, filed on Apr. 19, 2012.

(51) Int. Cl.
*A61B 90/00* (2016.01)
*A61B 18/00* (2006.01)

(52) U.S. Cl.
CPC ............ *A61B 2018/00904* (2013.01); *A61B 2018/00982* (2013.01); *A61B 2090/065* (2016.02); *A61B 2090/378* (2016.02)

(56) References Cited

U.S. PATENT DOCUMENTS

| | | |
|---|---|---|
| 5,267,997 A | 12/1993 | Farin |
| 5,788,636 A | 8/1998 | Curley |
| 5,836,990 A | 11/1998 | Li |
| 6,569,160 B1 | 5/2003 | Goldin |
| 6,663,623 B1 | 12/2003 | Oyama et al. |
| 7,160,296 B2 | 1/2007 | Pearson |
| 7,918,850 B2 | 4/2011 | Govari |
| 10,874,449 B2 * | 12/2020 | Budzelaar .............. A61B 18/12 |
| 2005/0261571 A1 | 11/2005 | Willis |
| 2007/0073282 A1 | 3/2007 | McGaffigan |
| 2007/0106147 A1 | 5/2007 | Altmann |
| 2010/0049188 A1 | 2/2010 | Nelson |
| 2010/0244868 A1 | 9/2010 | Cantave |
| 2010/0274239 A1 | 10/2010 | Saurav |
| 2011/0102266 A1 | 5/2011 | Folden |
| 2011/0130687 A1 | 6/2011 | Lin |
| 2012/0022355 A1 | 1/2012 | Byrd |
| 2012/0059286 A1 | 3/2012 | Hastings |

FOREIGN PATENT DOCUMENTS

| | | |
|---|---|---|
| JP | H108308851 A | 11/1996 |
| JP | H110185962 A | 7/1998 |
| JP | 2002372552 A | 12/2002 |
| JP | 2004097519 A | 4/2004 |
| KR | 20100078504 | 7/2010 |
| RU | 2285492 A | 6/2006 |
| WO | 2006038168 A1 | 4/2006 |
| WO | 2009065140 A1 | 5/2009 |

* cited by examiner

ENERGY APPLICATION APPARATUS

PRIORITY CLAIM

This application is a continuation of U.S. patent application Ser. No. 14/391,182 filed on Oct. 8, 2014, which is a Section 371 national phase application corresponding to Patent Cooperation Treaty application PCT/IB2013/052808 filed on Apr. 9, 2013, which claims priority to U.S. Provisional Application Ser. No. 61/635,357 filed on Apr. 19, 2012. Each of these documents is incorporated herein by reference.

FIELD OF THE INVENTION

The invention relates to an energy application apparatus, an energy application method and a computer program for applying energy to an object. The invention relates further to a sensing apparatus for sensing the object.

BACKGROUND

Catheter ablation is a minimally invasive procedure that is widely used for the treatment of cardiac arrhythmias. During a catheter ablation procedure cardiac tissue is locally destroyed, in order to block undesired conduction pathways. The local destruction can be achieved by hyperthermia using, for instance, a radio frequency (RF) source, a laser or a high-intensity focused ultrasound (HIFU) source as energy source or by hypothermia in case of cryoablation. The energy is generally provided via a tip of an ablation catheter. The ablation procedure can be monitored by a monitoring unit comprising a display unit, on which the monitoring result can be shown.

In order to allow a user like a physician to know when the ablation energy is actually applied, the energy source, for instance, an RF energy source, can be adapted to directly communicate with the monitoring unit, such that the monitoring unit can indicate on the display unit whether ablation energy is currently applied or not.

Interface and communication protocols generally vary depending on the respective manufacturer, the respective device and even depending on the respective version of the device, which can render a direct communication between an energy source for providing the ablation energy and the monitoring unit difficult.

SUMMARY

It is regarded as being an object of the present invention to provide an energy application apparatus, an energy application method and a computer program for applying energy to an object, and a sensing apparatus for sensing the object, which allow indicating whether energy is actually applied to the object or not, without necessarily requiring a communication to an energy application unit actually performing the energy application procedure.

In a first aspect of the present invention an energy application apparatus for applying energy to an object is presented, wherein the energy application apparatus comprises: an energy application unit for applying energy to the object, wherein the energy application unit is adapted to use electrical current for applying the energy, and a current measuring unit for measuring the electrical current used by the energy application unit and for providing a signal being indicative of whether the energy is applied to the object based on the measured electrical current.

Since the current measuring unit measures the electrical current used by the energy application unit and provides a signal being indicative of whether the energy is applied to the object based on the measured electrical current, a direct communication between the energy application unit and, for instance, a monitoring unit and/or a display unit for using and/or indicating the information whether energy is actually applied or not is not required.

The energy application apparatus is preferentially adapted to perform a cardiac ablation procedure, wherein the energy application unit is preferentially adapted to apply RF energy to cardiac tissue.

The current measuring unit is preferentially adapted to provide as the signal a binary signal indicating whether energy is applied or not based on the measured current.

The energy application unit comprises an electrical conductor through which the electrical current is flowing, wherein the current measuring unit is adapted to measure the current flowing through the electrical conductor, for example by using a current transformer, an antenna and/or a magnetic field sensor like a Hall sensor, in particular, a semiconductor Hall sensor. In particular, the current measuring unit can comprise a current transformer being integrated with the electrical conductor, wherein the current transformer comprises a primary element formed by the electrical conductor and a secondary element, which is preferentially electrically insulated from the primary element, and wherein the current measuring unit further comprises a measuring element for measuring the current at the secondary element and for providing the signal based on the current measured at the secondary element. This allows reliably determining the current and thus whether energy is applied or not.

The secondary element of the current transformer is preferentially a coil being wound around a magnetic core of the current transformer enclosing the electrical conductor which forms the primary element of the current transformer. Preferentially, the current transformer is configured such that current flowing through the secondary element comprises a current waveform being similar to the current waveform of the current flowing through the primary element, wherein the current flowing through the secondary element has an amplitude being smaller than the amplitude of the current flowing through the primary element.

In an embodiment the secondary element is adapted to be attachable to the electrical conductor for forming the current transformer. For instance, the secondary element and one or several other elements of the current transformer like the magnetic core can be physically clipped to the electrical conductor, which forms the primary element of the current transformer, for forming the current transformer. The secondary element and the one or several other elements, except for the electrical conductor forming the primary element, may therefore be attached to an existing energy application apparatus for measuring the current. This attaching to the electrical conductor is preferentially performed in a detachable way by using, for instance, the clipping mechanism, in order to allow the current measuring functionality to be used with different energy application apparatuses.

Preferentially the current measuring unit is adapted to measure current having predefined parameters and to provide the signal based on whether a current having the predefined parameters has been measured. For instance, the current measuring unit can be adapted to detect whether a current is present having parameters within predefined parameter ranges and to provide a binary signal being indicative of whether this current has been detected. In an embodiment, the predefined parameter ranges define current amplitudes and current frequencies. In particular, the current measuring unit can be adapted to detect whether a current is present having an amplitude between 0.1 and 2.0 A, further preferred between 0.13 and 1.8 A, and having a frequency between 400 and 500 kHz and to provide a corresponding binary signal. This reduces the likelihood that an application of energy is wrongly indicated, because a current has been measured, which is not the current used by the energy application unit for applying energy to the object, i.e. the likelihood is reduced that an external interference signal is mistakenly detected as a current applied by the energy application unit.

The energy application apparatus is preferentially an ablation apparatus for ablating tissue within a living being, which is adapted to form, in operation, an ablation loop comprising a) a power source for providing RF power, b) an ablation catheter comprising an ablation electrode for applying the energy to the tissue, c) a first electrical connection electrically connecting the power source with the ablation catheter and being, for instance, a wire or a cable, d) an indifferent electrode for being placed at the outside of the living being, and e) a second electrical connection electrically connecting the indifferent electrode with the power source and being, for example, a wire or a cable, wherein the current measuring unit is located in the ablation loop for measuring the electrical current. In particular, the current measuring unit can be integrated within the ablation loop such that it forms a physical part of the ablation loop.

The current measuring unit can be placed for, for instance, measuring the current in the first electrical connection, in the second electrical connection or in the ablation catheter, in particular, inside a catheter handle. Correspondingly, the current measuring unit may be placed at the first electrical connection or at the second electrical connection, or the current measuring unit may be placed inside or around the catheter handle. In particular, the current measuring unit can be a physical part of, for instance, the first electrical connection, the second electrical connection or the ablation catheter.

The electrical current used by the energy application unit generates electromagnetic radiation, wherein the current measuring unit can comprise a receiving element for receiving the electromagnetic radiation, wherein the current measuring unit can be adapted to measure the current based on the received electromagnetic radiation. This allows measuring the current over a relatively large distance, wherein the measuring unit does not need to be in physical contact with, for instance, a wire or cable through which the current is flowing.

The receiving element is preferentially an antenna, in particular, a simple loop antenna. The antenna may not be very selective, i.e., for instance, it may be adapted to receive electromagnetic radiation within a frequency range of 400 to 5000 kHz.

In another embodiment the current measuring unit comprises a magnetic field sensor for measuring a magnetic field generated by the electrical current used by the energy application unit, wherein the current measuring unit is adapted to measure the current based on the measured magnetic field. The magnetic field sensor is preferentially a Hall sensor.

The energy application apparatus may further comprise an output unit for indicating to a user whether the energy is applied based on the signal provided by the current measuring unit. The output unit is preferentially a display unit for displaying a corresponding indication. In particular, the display unit can be adapted to display the beginning and the end of the application of energy.

The energy application apparatus preferentially further comprises a sensing unit for sensing the object, thereby generating a sensing result, wherein the display unit can be adapted to also show the sensing result. In a preferred embodiment the sensing unit is adapted to ultrasonically sense the object such that an M-mode image is generated, wherein the display unit can be adapted to display the generated M-mode image together with energy application indications indicating at least one of the beginning and the end of the application of energy based on the provided signal. This allows a user like a physician to readily see on the display unit which part of the M-mode image corresponds to an energy application period, during which the energy is applied to the object, and which part of the M-mode image does not correspond to the energy application period.

The sensing unit can also be adapted to perform the sensing of the object depending on the provided signal being indicative of whether the energy is applied. Preferentially, the sensing unit is adapted to sense the object, if the signal indicates that energy is not applied to the object. In particular, the signal can be indicative of energy application periods, in which the energy is applied and thus the current is measured, and non energy application periods, in which the energy is not applied and thus the current is not measured, wherein the sensing unit can be adapted to sense the object only in non energy application periods. This reduces generally possible disturbances of the sensing of the object by the application of energy, in particular, a corresponding generally possible interference can be prevented.

In a further aspect of the present invention a sensing apparatus for sensing an object is presented, wherein the sensing apparatus comprises: a sensing unit for sensing the object, thereby generating a sensing result, a current measuring unit for measuring electrical current used by an energy application unit for applying energy to the object and for providing a signal being indicative of whether the energy is applied to the object based on the measured electrical current, and an output unit for outputting the sensing result and for indicating whether energy is applied to the object based on the signal provided by the current measuring unit.

In a further aspect of the present invention an energy application method for applying energy to an object is presented, wherein the energy application method comprises: applying energy to the object by an energy application unit, wherein the energy application unit uses electrical current for applying the energy, measuring the electrical current used by the energy application unit and providing a signal being indicative of whether the energy is applied to the object based on the measured electrical current by a current measuring unit.

In a further aspect of the present invention a computer program for applying energy to an object is presented, wherein the computer program comprises program code means for causing an energy application apparatus as defined in claim 1 to carry out the steps of the energy application method as defined in claim 14, when the computer program is run on a computer controlling the energy application apparatus.

It shall be understood that the energy application apparatus of claim 1, the sensing apparatus of claim 13, the energy application method of claim 14 and the computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION

Figure 1:
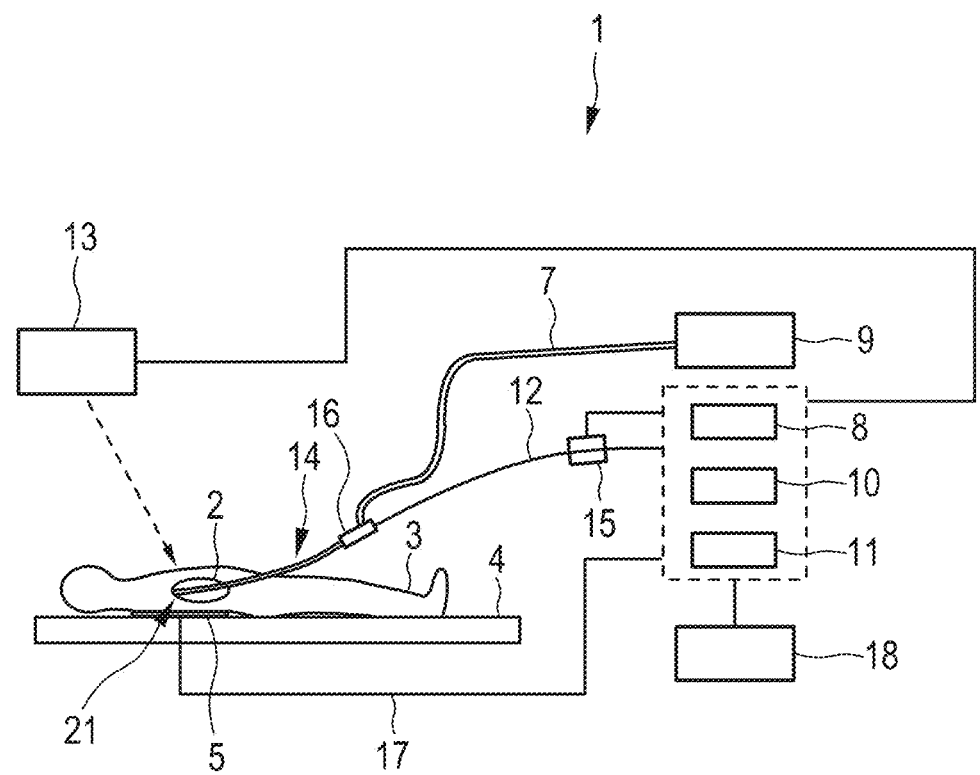
FIG. 1 shows schematically and exemplarily an embodiment of an energy application apparatus for applying energy to an object.
Figure 2:
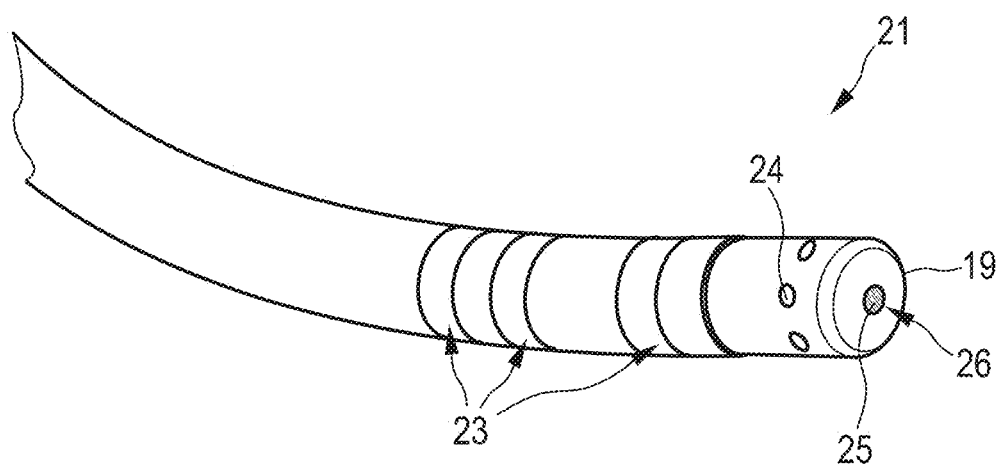
FIG. 2 shows schematically and exemplarily an embodiment of a tip of a catheter of the energy application apparatus, FIG. 3 schematically and exemplarily shows an embodiment of an ablation loop with a current measuring unit of the energy application apparatus.

FIG. 1 shows schematically and exemplarily an embodiment of an energy application apparatus 1 for applying energy to an object. In this embodiment, the energy application apparatus 1 is a cardiac ablation apparatus for performing a cardiac ablation procedure, which comprises an ablation catheter 14 with a catheter handle 16. The tip 21 of the ablation catheter 14 has been introduced into a heart 2 of a person 3 lying on a table 4. The catheter tip 21 is exemplarily shown in more detail in FIG. 2.

The catheter tip 21 comprises an ablation electrode 19 formed as a cap electrode with irrigation openings 24 and a sensing opening 26. The irrigation openings 24 are arranged along the circumference of the cap electrode 19 and the sensing opening 26 is arranged centrally in the frontal surface of the cap electrode 19. An ultrasound transducer 25 is located within the cap electrode 19 at the opening 26 such that cardiac tissue can be ultrasonically sensed through the sensing opening 26 by the ultrasound transducer 25.

The catheter tip 21 further comprises sensing electrodes 23, which are formed as ring electrodes. The sensing electrodes 23 are used for measuring electrical cardiac signals.

The catheter 14 is connected to an RF power source 8, an ultrasound sensing control unit 10 and an electrical sensing measuring unit 11 via a cable 12. The cable 12 and the catheter 14 comprise several insulated wires for electrically connecting the sensing electrodes 23 with the electrical sensing measuring unit 11, the ablation electrode 19 with the RF power source 8 and the ultrasound transducer 25 with the ultrasound sensing control unit 10. In this embodiment, the ultrasound sensing control unit 10 is adapted to generate in cooperation with the ultrasound transducer 25 M-mode images of the cardiac tissue to which energy is applied, i.e. which is ablated. The sensing electrodes 23 and the electrical sensing measuring unit 11 are adapted to measure electrical cardiac signals, in particular, to measure electrocardiography signals, and the RF power source 8 and the ablation electrode 19 are adapted to ablate the cardiac tissue.

The ablation electrode 19 and the RF power source 8 form an energy application unit for applying energy to the object being, in this embodiment, cardiac tissue, wherein the energy application unit 8, 19 is adapted to use electrical current for applying the energy. The ultrasound transducer 25 and the ultrasound sensing control unit 10 form a sensing unit for sensing the cardiac tissue.

The energy application apparatus 1 further comprises an indifferent electrode 5 being placed at the back of the person 3, which is connected with the RF power source 8 via a further cable 17. The RF power source 8, the ablation catheter 14, the cable 12, which can be regarded as being a first electrical connection electrically connecting the RF power source 8 with the ablation catheter 14, the person 3, the indifferent electrode 5, and the further cable 17, which can be regarded as being a second electrical connection electrically connecting the indifferent electrode 5 with the RF power source 8, form an ablation loop, in which a current measuring unit 15 is located, in particular, integrated. The current measuring unit 15 is adapted to measure the electrical current used by the ablation catheter 14 for ablating the cardiac tissue and to provide a signal being indicative of whether the energy is actually applied to the cardiac tissue based on the measured electrical current. In this embodiment, the current measuring unit is adapted to measure RF current, if present, and to provide a binary signal indicating whether the cardiac tissue is actually ablated or not based on whether RF current is measured or not.

Figure 3:
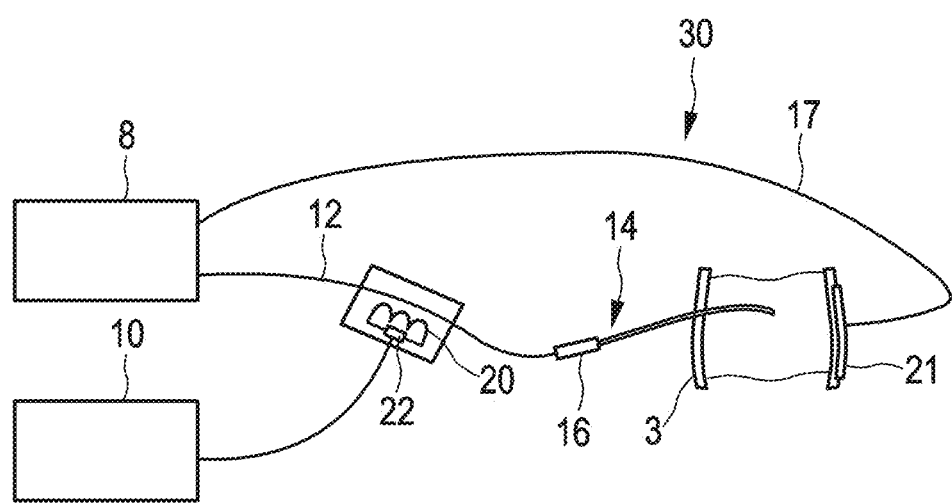

The current measuring unit 15 is adapted to measure the RF current flowing through an electrical conductor within the ablation loop being, in this embodiment, the cable 12 connecting the ablation catheter 14 with the RF power source 8. The current measuring unit 15 comprises, in this embodiment, a current transformer being integrated with the cable 12, wherein the current transformer comprises a primary element formed by the cable 12 and a secondary element 20 as schematically and exemplarily shown in FIG. 3. FIG. 3 only shows the ultrasound sensing control unit 10 and the ablation loop 30, which is formed by the RF power source 8, the ablation catheter 14, the cable 12 connecting the RF power source 8 and the ablation catheter 14 and having integrated the current measuring unit 15, the person 3, the indifferent electrode 5 and the cable 17 connecting the indifferent electrode 5 and the RF power source 8.

The current measuring unit 15 further comprises a measuring element 22 for measuring the current at the secondary element 20 and for providing the signal based on the current measured at the secondary element 20.

The secondary element 20 is a coil being wound around a magnetic core of the current transformer enclosing the cable 12 which forms the primary element of the current transformer. The current transformer is configured such that current flowing through the secondary element comprises a current waveform being similar to the current waveform of the current flowing through the primary element, wherein the current flowing through the secondary element has an amplitude being smaller than the amplitude of the current flowing through the primary element. The primary element 12 and the secondary element 20 are electrically insulated from each other.

The measuring element 22 can comprise an ampere meter for measuring the current at the secondary element 20 and an electrical circuit being configured to generate a binary signal indicating whether RF current has been measured or not, i.e. indicating whether cardiac ablation is actually performed or not. In other embodiments, the current measuring functionality and/or the signal generating functionality can be provided by another element, which can be a part of, for instance, the ultrasound sensing control unit 10. For instance, an electrical circuit of the ultrasound sensing control unit 10 can be configured to generate the binary signal depending on the current measured at the secondary element of the current transformer. In this case, the current transformer together with this electrical circuit of the ultrasound sensing control unit forms the current measuring unit for measuring the electrical current used by the energy application unit and for providing a signal being indicative of whether the energy is applied to the object based on the measured electrical current.

The secondary element 20 together with the magnetic core and the measuring element 22 can be adapted to be attachable to the cable 12 for forming the current transformer. For instance, the secondary element 20, the magnetic core and the measuring element 22 of the current transformer can be physically clipable to the cable 12, which forms the primary element of the current transformer, for forming the current transformer. The secondary element together with the other elements of the current transformer, except for the cable 12 forming the primary element, may therefore be attachable to an existing cardiac ablation apparatus for measuring the RF current. Moreover, the secondary element together with the other elements of the current transformer, except for the primary element formed by the cable 12, may also be easily detachable from the cable 12, in order to allow the RF current measuring functionality to be used with different energy application apparatuses. The current measuring unit 15 can also be adapted to be attachable to another part of the ablation loop 30. Furthermore, the current measuring unit 15 can also be physically integrated within the ablation loop 30 such that it forms a physical part of the ablation loop.

The current measuring unit 15 can be, particularly detachably, attached to or physically integrated into the cable 12 connecting the ablation catheter 14 with the RF power source 8 as schematically and exemplarily shown in FIGS. 1 and 3, the cable 17 connecting the indifferent electrode 5 with the RF power source 8, or the ablation catheter 14, in particular, inside or around the catheter handle 16.

The current measuring unit 15 is adapted to measure current having predefined parameters and to provide the signal based on whether a current having the predefined parameters has been measured. In particular, the current measuring unit 15 is adapted to detect whether an RF current is present having parameters within predefined parameter ranges and to provide a binary signal being indicative of whether this RF current has been detected. In this embodiment, the current measuring unit 15 is adapted to detect whether a current is present having an amplitude between 0.1 and 2.0 A, further preferred between 0.13 and 1.8 A, and having a frequency between 400 and 500 kHz, wherein the generated binary signal indicates that the cardiac ablation is actually performed, if such an RF current is measured.

The energy application apparatus 1 further comprises an output unit 18 being, in this embodiment, a display unit for displaying the M-mode image generated by the ultrasound transducer 25 and the ultrasound sensing control unit 10 and for indicating to a user like a physician whether the energy is applied based on the signal provided by the current measuring unit 15.

Figure 4:
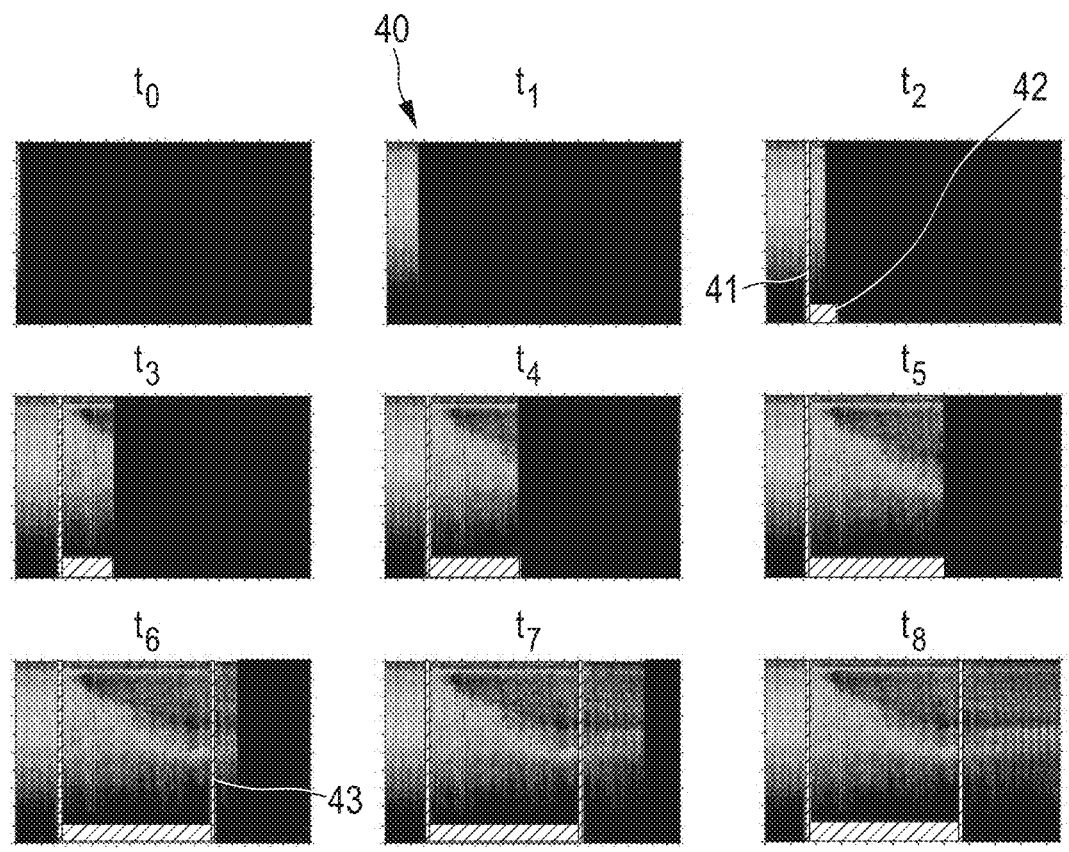
FIG. 4 shows an M-mode image at different points in time showing cardiac tissue, wherein the beginning and the end of applying energy to the cardiac tissue are indicated.

FIG. 4 shows schematically and exemplarily an M-mode image 40 for different points in time t0 . . . t8. The ultrasound transducer 25 together with the ultrasound sensing control unit 10 continuously acquires A-lines, which are appended to previously acquired A-lines for generating an M-mode image 40, in which the number of A-lines increases with increasing time. If the current measuring unit 15 detects RF current in the cable 12 and generates a signal indicating that RF energy is applied to the cardiac tissue, the display unit 18 shows a first energy application indication 41 being, in this embodiment, a colored vertical line for indicating the beginning of the application of the RF energy to the cardiac tissue. During the application of the energy to the cardiac tissue a bar 42 grows in accordance with the growing M-mode image, wherein, if the signal provided by the current measuring unit 15 indicates that the application of the energy to the cardiac tissue has been stopped, a second energy application indication 43 indicates that the ablation procedure has been stopped. In this embodiment, also the second energy application indication 43 is a vertical line within the M-mode image.

In FIG. 4, the first energy application indication 41 indicating the beginning of the application of energy is firstly shown in the M-mode image at the time point t2 and the second energy application indication 43 is firstly shown in the M-mode image at the time point t6. In FIG. 4 the vertical axis of an M-mode image at a certain point in time indicates the depth within the cardiac tissue, wherein the downward direction indicates the direction of increasing depths within the cardiac tissue for the respective point in time.

Since the energy application indications 41, 43 are shown at the respective temporal positions within the M-mode image on the display unit 18, a user like a physician can easily see on the display unit 18 which part of the M-mode image corresponds to an energy application period, during which the energy is applied to the cardiac tissue, and which part of the M-mode image does not correspond to the energy application period.

In an embodiment, the ultrasound sensing control unit 10 may be adapted to control the ultrasound sensing such that it is not performed, if the signal provided by the current measuring unit 15 indicates that the energy is not applied to the cardiac tissue. In particular, the signal is indicative of energy application periods, in which the energy is applied and thus the RF current is measured, and of non-energy application periods, in which the energy is not applied and thus the current is not measured, wherein the ultrasound sensing control unit 10 may be adapted to control the ultrasound sensing such that it is only performed in non-energy application periods. This can reduce generally possible disturbances of the ultrasound sensing of the cardiac tissue by the application of energy.

The energy application apparatus 1 further comprises an irrigation control unit 9 like an irrigation pump, which is connected with the catheter 14 by a tube 7 for pumping irrigation fluid into the catheter such that it can leave the catheter tip 21 through the irrigation openings 24. Moreover, the energy application apparatus 1 comprises a localization unit 13 for localizing the tip 21 of the ablation catheter 14 within the heart 2 of the person 3. The localization unit 13 can be any known localization unit like an X-ray fluoroscopy unit, an electromagnetic localization unit, et cetera. Also the determined position of the catheter tip 21 within the heart 2 of the person 3 can be shown on the display unit 18 for allowing the user to verify the ablation location at which the energy is applied to the cardiac tissue.

Figure 5:
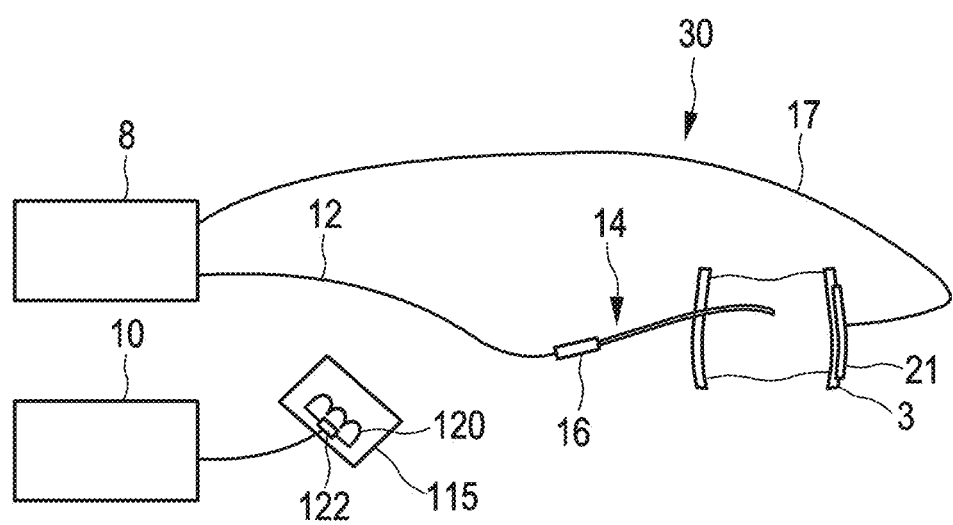
FIG. 5 shows a further embodiment of an ablation loop and a separate current measuring unit.

Although in the embodiments described above with reference to FIGS. 1 and 3 the current measuring unit 15 is attached, in particular, clipped to the ablation loop 30 or physically integrated into the ablation loop 30 such that it forms a physical part of the ablation loop 30, in other embodiments the current measuring unit can also be separated from the ablation loop 30 as schematically and exemplarily shown in FIG. 5.

In FIG. 5, the current measuring unit 115 comprises a receiving element 120 for receiving electromagnetic radiation generated by the electrical RF current flowing through the ablation loop 30, wherein the current measuring unit 115 is adapted to measure the current based on the received electromagnetic radiation. This allows measuring the RF current over a relatively large distance, wherein the measuring unit 115 does not need to be in physical contact with, for instance, a wire or a cable through which the RF current is flowing.

The receiving element 120 is an antenna, in particular, a simple loop antenna. The antenna 120 is not very selective and is adaptive to receive electromagnetic radiation within a frequency range of 400 to 5000 kHz. Similar to the measuring element 22 described above with reference to FIG. 3, also the current measuring unit 115 comprises a measuring element 122 for measuring the current induced in the antenna 120 and for providing a binary signal being indicative of whether the current measuring unit 115 has detected that RF current is flowing through the ablation loop 30 or not.

The ultrasound sensing part of the energy application apparatus, the current measuring unit and the display unit can be regarded as forming a sensing apparatus for sensing an object, wherein due to the current measuring unit information about whether energy is applied or not can be shown on the display unit. The sensing apparatus can be an integrated apparatus, i.e. integrated with the energy application apparatus, or it can be a separate apparatus. In other embodiments the sensing apparatus can also be adapted to perform another kind of sensing, for example, an electrical sensing, an optical sensing, et cetera.

Figure 6:
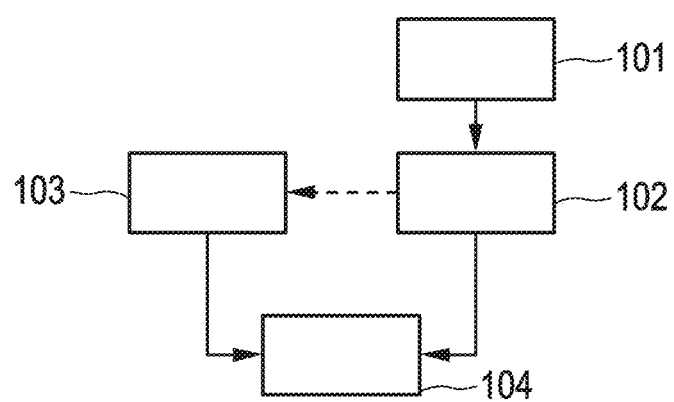
FIG. 6 shows a flowchart exemplarily illustrating an embodiment of an energy application method for applying energy to an object.

In the following an embodiment of an energy application method for applying energy to an object will exemplarily be described with reference to a flowchart shown in FIG. 6.

In step 101, energy is applied to the cardiac tissue by the RF power source 8 via the ablation catheter 14, wherein RF current is used for applying the energy. In step 102, the electrical current is measured by the current measuring unit 15, 115 and a signal is generated being indicative of whether the energy is applied to the cardiac tissue based on the measured RF current. Thus, in step 102 preferentially a binary signal is generated and provided, which indicates whether the cardiac tissue is actually ablated or not depending on whether RF current is detected or not. In step 103, which can be performed before, during and/or after the energy is applied to the object, the ultrasound transducer 25 together with the ultrasound sensing control unit 10 generates M-mode images 103. In step 104, the generated M-mode images and energy application indications indicating whether energy is actually applied to the object or not are shown on the display unit 18. Optionally, the signal generated and provided in step 102 can be used in step 103 by the ultrasound sensing control unit 10 for controlling the ultrasound sensing such that the ultrasound sensing is performed only in non-energy application periods, in which the energy is not applied to the object.

It should be noted that steps 101 to 104 can be performed substantially simultaneously, wherein with using the RF current for applying the energy this RF current is measured, a corresponding signal being indicative of whether energy is applied to the cardiac tissue is generated based on the measured RF current, and corresponding energy application indications indicating whether energy is actually applied or not are shown on the display unit together with simultaneously generated M-mode images.

The RF ablation catheter with integrated ultrasonic lesion monitoring and fluid irrigation allows the visualization of the progression of the lesion boundary preferentially in realtime. In particular, the ablation catheter comprises one or more ultrasound transducers arranged within the catheter tip and connected to an external console, i.e. to the ultrasound sensing control unit, wherein the ultrasound sensing control unit together with the display unit may be regarded as being a cardiac ablation monitoring (CAM) unit.

The energy application apparatus is preferentially adapted to indicate to a surgeon on an ultrasound image that is displayed in realtime when ablation is taking place. The surgeon may control the application of the ablation energy, for instance, by means of a foot pedal connected to the RF power source 8, wherein the indication, i.e. the energy application indication, shown on the display is preferentially a direct feedback of this actually happening.

Although in the above described embodiments the signal, which is indicative of whether energy is actually applied to the object or not, is used for indicating on the display unit when energy is actually applied and/or to control an ultrasound sensing procedure depending on whether energy is actually applied to the object, in other embodiments the signal can also be used for other purposes. For instance, in other embodiments the energy application apparatus can further be adapted to determine ablation parameters like the ablation depth, which is the depth of the progressing lesion in the tissue, based on the ultrasound images and the knowledge about whether energy is actually applied to the tissue or not.

Generally, the information on ablation power could be obtained from the RF generation, i.e. from the RF power source, directly by communication between the energy application unit and the ultrasound sensing control unit, in particular a CAM console comprising the ultrasound sensing control unit and the display unit. However, interface communication protocols can vary per manufacturer, device and even device version. A communication between, for instance, an RF power source and a CAM console is therefore not desired. It could also be possible to extract the information about whether ablation power is present or not from features introduced into the ultrasound signal due to RF energy delivery, i.e. it could be made use of the otherwise unwanted RF interference on the ultrasound signal. But, this option does not yield reliable results, because the interference levels are not known and because generally design steps are taken to make the ablation monitoring system highly insensitive to external disturbances like the RF interference.

Moreover, generally the interference should be kept as small as possible. The energy application apparatus described above with reference to FIGS. 1 to 6 provides therefore a solution to detect whether ablation power is applied or not, without needing a direct communication between the RF power source and, for instance, the ultrasound sensing control unit 10, in particular, the CAM console, and without needing an extraction of RF interference from ultrasound signals. In fact, preferentially the energy apparatus allows reliably detecting whether ablation power is applied or not, without requiring any communication to the ablation loop, and the detection of whether ablation power is applied or not is independent of the respective manufacturer, device and device version.

The energy application apparatus is preferentially adapted to detect from the respective cable that carries the RF current whether RF ablation is on or not. This binary information can be used to indicate RF energy delivery on the display unit, in particular, on the CAM console, without any direct communication to the ablation loop. The detection is preferentially based on the electromagnetic field, which a wire generates, when it carries ablation currents. It makes preferentially use of the fact that the respective wire, at which the RF current is measured, is part of a large loop that includes the ablation generator, i.e. the RF power source, the cable from the ablation generator to the ablation catheter, the ablation catheter, the person, the indifferent electrode at the back of the person and finally the cable or wire from the indifferent electrode to the ablation generator. Due to this ablation loop the ablation current through the respective wire creates a relatively strong electromagnetic field that is relatively easy to detect. For this detection a current transformer can be used, that is located somewhere in the ablation current loop. For instance, the current transformer can be located at the cable from the RF power source to the ablation catheter, at the cable from the RF power source to the indifferent electrode, or the current transformer can be placed inside or around the catheter handle. The primary side of the current transformer is preferentially formed by the respective wire carrying the ablation current. Preferentially, the ablation wire does not need to be modified, cut or connected to make it part of the current transformer, as the other parts of the current transformer can be assembled around the respective wire carrying the ablation current. The ablation current introduces a small signal at a secondary side of the current transformer that is a relative copy of the ablation current waveform, but with different amplitude. The primary and secondary sides of the current transformer are electrically insulated. The secondary side of the current transformer is preferentially formed by a coil wound around a magnetic core. A detection circuit, i.e. a measuring element, at the secondary side senses, if an ablation current is present or not. The RF power is preferentially kept stable regardless of the load. The RF power is preferentially in the range of 5 to 100 W, and the loads are preferentially in a range of 30 to 300Ω. Since $I=\sqrt{P/R}$, wherein I is the ablation current, P is the power provided by the RF power source and R are the loads, the ablation currents are preferentially in the range of 0.13 to 1.8 A. Furthermore, the ablation frequencies, i.e. the frequencies of the ablation current, are preferentially within the range of 400 to 500 kHz. Therefore, the detection circuit is preferentially designed to detect currents in these specified ranges, thereby providing a reliable status indication indicating whether ablation is taking place or not.

Since the electromagnetic radiation emitted by the respective wire carrying the ablation current is quite significant, sensing can be done at a relatively large distance. Therefore, the sensor, i.e. the current measuring unit, does not need to be in contact with the respective wire or does not even lead to be close to it. For larger distances the main concern would be false detections, for instance, by other ablation systems operating in adjacent operating rooms. Due to the characteristics of the respective energy application apparatus, which is defined by, for instance, the frequency and the ablation loop, the magnetic radiation is dominant and a simple loop antenna can be used to detect the ablation current. Due to variations in the ablation frequency the antenna does not need to be very selective. For instance, the antenna can be adapted to receive signals within the frequency range of 400 to 5000 kHz. However, the antenna is preferentially tuned to the ablation frequency.

Instead of or in addition to an antenna the current measuring unit can also comprise a magnetic field sensor for sensing a magnetic field generated by the electrical current used by the energy application unit, wherein the current measuring unit can be adapted to measure the current based on the measured magnetic field. The magnetic field sensor is preferentially a Hall sensor.

The energy application unit can be adapted to continuously apply the energy to the object or to apply the energy to the object in a pulsed way. In the latter case the ablation activity can be regularly interrupted to allow the monitoring equipment, i.e. the ultrasound sensing control unit and the ultrasound transducer, to measure without RF interference. Thus, the ablation and the ultrasound sensing can be coordinated such that the object is ultrasonically sensed, when the RF power source does not provide the ablation pulse.

Although in the above described embodiments the signal, which is indicative of whether energy is applied or not, is used for indicating this information to a user on a display unit and to control the ultrasound sensing procedure based on whether energy is actually applied or not, in other embodiments the detection whether RF ablation is actually on or off can also be used for other purposes. For instance, analyzing ultrasound data can depend on whether energy is actually applied or not, i.e. parameters of corresponding analyzing algorithms may be situation specific. For example, a respective analyzing algorithm can be adapted to filter out ultrasound artifacts occurring in the first few seconds after it has been indicated that energy application has been started.

Although in above described embodiments an indication is provided whether energy is actually applied or not on a display unit showing an ultrasound image, in another embodiment such an indication can also be shown together with other information. For instance, corresponding indications can be shown together with electrogram recordings, which may be provided by an electrophysiological (EP) recording system. The electrogram recordings may be intracardiac recordings measured with ablation and diagnostic catheters as well as body surface electrograms. The energy application indications may also be shown together with an electroanatomical map provided by an electroanatomical mapping system, for instance, an impedance-based system like NavX from the company St. Jude Medical or an electromagnetic-based system like Carto from the company Biosense Webster. The energy application indications can also be shown together with one or several images like a live x-ray image or a live two-dimensional or three-dimensional ultrasound image. The energy application indications may be shown as a text like "RF on" and "RF off" or, for example, an ablation tip may be shown on the respective image in a color, for instance, in red indicating that energy application is on. Energy applications may also be shown on other kind of images like magnetic resonance images. Also on a display unit of contact force sensing systems like fiber-optics based systems from the company Endosense, like electromagnetic based systems such as SmartTouch from the company Biosense Webster, or like electrical coupling index based or impedance based systems from the company St. Jude Medical the indication whether energy is actually applied or not may be shown. Moreover, on display units of endoscopic ablation systems like IRIS ballon from the company Voyage Medical the indication may be shown, or on a display unit of an EP navigator of the company Philips, in particular, on a display unit showing a pre-acquired three-dimensional image with a live x-ray image.

Although in an above described embodiment the ablation catheter comprises a single ultrasound transducer only, in other embodiments the ablation catheter can also comprise several ultrasound transducers for sensing the object through corresponding sensing openings in the tip of the ablation catheter. The one or several ultrasound transducers can be one-dimensional or two-dimensional phased array ultrasound transducers.

Although in above described embodiments the energy application apparatus is adapted to ablate cardiac tissue, in other embodiments the energy application apparatus can also be adapted to ablate other kinds of tissue, for instance, tissue of other organs. Moreover, the energy application apparatus can also be adapted to apply energy to another object not being tissue of an organ. For example, the energy application apparatus can be adapted to apply energy to a technical object.

Although in the above described embodiments the energy is applied to the object via a tip of a catheter, in other embodiments the energy can also be applied via another element like a tip of an interventional needle or via an electrode located at another element.

Although in above described embodiments the catheter tip comprises irrigation openings, in other embodiments the catheter tip may not comprise irrigation openings.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Steps like the measurement of the current, the generation of the signal being indicative of whether energy is applied or not, the control of the ultrasound sensing procedure depending on the signal, et cetera performed by one or several units or devices can be performed by any other number of units or devices. One or several of these steps and/or the control of the energy application apparatus in accordance with the energy application method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

What is claimed is:

1. An apparatus, comprising:
    an ablation catheter comprising:
        an ablation electrode configured to ablate an object when energy is applied to the object using an electrical current; and
        an ultrasound transducer configured to generate ultrasound image data; and
    a computer configured for communication with the ablation catheter, wherein the computer is configured to:
        receive a binary signal indicative of whether the energy is applied to the object based on a measurement of the electrical current;
        receive the ultrasound image data from the ultrasound transducer; and
        output to a display in communication with the computer:
            an ultrasound image based on the ultrasound image data, wherein the ultrasound image data is representative of the object over time; and
            an energy application indication positioned at a corresponding temporal position on the ultrasound image and configured to indicate when the energy is applied to the object based on the binary signal.

2. The apparatus of claim 1, further comprising:
    an ampere meter configured to measure the electrical current flowing in a secondary coil wound around a magnetic core of a transformer, wherein a primary element of the transformer is a cable that delivers the energy to the ablation electrode.

3. The apparatus of claim 2, wherein the ampere meter determines whether the energy is being applied by detecting whether RF current is present in the measured electrical current.

4. The apparatus of claim 1, further comprising:
    an electrical conductor and an electrical circuit in communication with the electrical conductor, wherein the electrical conductor is adapted to measure current having predefined parameters, wherein the electrical circuit provides the binary signal based on whether a current having the predefined parameters has been measured, wherein the electrical conductor is any one or more of: a current transformer, an antenna, a magnetic field sensor, or an ampere meter.

5. The apparatus of claim 1, wherein the apparatus is adapted to form, in operation, an ablation loop comprising:
    a power source of radio frequency power;
    the ablation catheter comprising an ablation electrode configured to apply the energy to tissue;
    a first electrical connection electrically connecting the power source with the ablation catheter;
    an indifferent electrode configured to be placed outside of a body of a patient; and
    a second electrical connection electrically connecting the indifferent electrode with the power source, wherein an electrical conductor is located in the ablation loop for measuring the electrical current.

6. The apparatus of claim 1, further comprising:
    an antenna,
    wherein the electrical current used by the ablation electode generates electromagnetic radiation, wherein the antenna comprises a receiving element configured to receive the electromagnetic radiation, wherein the antenna is adapted to measure the electrical current based on the received electromagnetic radiation.

7. The apparatus of claim 1, further comprising:
    a magnetic field sensor,
    wherein the electrical current used by the ablation electrode generates a magnetic field, wherein the magnetic field sensor is configured to measure the magnetic field, wherein the magnetic field sensor is adapted to measure the electrical current based on the measured magnetic field.

8. The apparatus of claim 1, further comprising:
    a sensor configured to sense the object, wherein the sensor is adapted to perform the sensing of the object in response to the binary signal indicating that the energy is being applied to the object.

9. The apparatus of claim 1, further comprising:
    a sensor configured to sense the object, wherein the sensor is adapted to perform the sensing of the object in response to the binary signal indicating that the energy is not being applied to the object.

10. The apparatus of claim 1, wherein the binary signal indicates that ablation is being performed when a current having a frequency between about 400 MHz and about 500 MHz is detected.

11. The apparatus of claim 1, wherein the binary signal indicates that ablation is being performed when a current having a magnitude between about 0.1-2.0 A is detected.

12. The apparatus of claim 1, wherein the binary signal indicates that ablation is being performed when a current having a magnitude between about 0.1-2.0 A and a frequency between about 400 MHz and about 500 MHz is detected.

13. The apparatus of claim 1, wherein the ultrasound image comprises an M-mode ultrasound image.

14. The apparatus of claim 1, further comprising:
a current transformer in communication with the ablation catheter, wherein the current transformer is configured to measure electrical current used by the ablation catheter and to provide a binary signal indicative of whether the energy is applied to the object based on the measured electrical current.

\* \* \* \* \*